US006572577B1

(12) United States Patent
Binner et al.

(10) Patent No.: US 6,572,577 B1
(45) Date of Patent: Jun. 3, 2003

(54) APPLICATOR FOR CATAMENIAL DEVICE HAVING IMPROVED GRIPPER END

(75) Inventors: Curt Binner, Somerset, NJ (US); Gary Vogt, Newtown, PA (US); Linda M. Pierson, Somerville, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 09/602,950

(22) Filed: Jun. 23, 2000

(51) Int. Cl.[7] ............................................. A61F 13/20
(52) U.S. Cl. ..................................................... 604/15
(58) Field of Search ......................... 604/11–18, 57–60

(56) References Cited

U.S. PATENT DOCUMENTS

| 3,042,040 | A | * | 7/1962 | Galik ........................ 604/15 |
| 3,297,031 | A | * | 1/1967 | Bray ......................... 604/59 |
| 3,347,234 | A | | 10/1967 | Voss |
| 3,433,225 | A | | 3/1969 | Voss et al. |
| 3,572,339 | A | | 3/1971 | Voss et al. |
| 3,575,169 | A | | 4/1971 | Voss et al. |
| 3,683,759 | A | | 8/1972 | Voss et al. |
| 4,048,998 | A | | 9/1977 | Nigro |
| D250,663 | S | | 12/1978 | Koch et al. |

(List continued on next page.)

FOREIGN PATENT DOCUMENTS

| EP | 0291 343 | 11/1988 |
| EP | 0 392 281 | 10/1990 |
| EP | 048148 B1 | 4/1992 |
| EP | 0 605 016 | 12/1993 |
| GB | 1108291 | 4/1968 |
| GB | 1272863 | 5/1972 |
| GB | 1272864 | 5/1972 |
| GB | 2166656 | 5/1986 |
| WO | WO 91/06272 | 5/1991 |
| WO | WO 01/00126 | 1/2001 |
| ZA | 7208833 | 9/1973 |

OTHER PUBLICATIONS

McNeil, PPC, Inc., PCT/US01/20208, Search Report.

*Primary Examiner*—Dennis Ruhl

(57) ABSTRACT

The present invention relates to applicators for inserting objects into body cavities, and to methods for making the same. The applicators are particularly useful for inserting catamenial and prophylactic devices into a vaginal canal. The applicators comprise a tubular insertion member and a retrofitted gripping member. The gripping member has an outer diameter greater than that of the insertion member. An interface is created due to this size differential, which provides a visual or tactile cue of applicator insertion depth, and thereafter object positioning within the body cavity. The gripping member comprises at least one raised area on its outwardly disposed surface, providing resistance to movement of the user's manual digit in response to longitudinal forces on the insertion member. Longitudinal forces are created during both the insertion step of use, as well as the expulsion step delivering the contained object from the insertion member into the body cavity.

18 Claims, 14 Drawing Sheets

U.S. PATENT DOCUMENTS

| | | |
|---|---|---|
| 4,198,978 A | 4/1980 | Nigro |
| 4,329,991 A | 5/1982 | Sakurai |
| 4,361,150 A | 11/1982 | Voss |
| 4,447,222 A | 5/1984 | Sartinoranont |
| 4,508,531 A | 4/1985 | Whitehead |
| 4,573,963 A | 3/1986 | Sheldon |
| 4,573,964 A | 3/1986 | Huffman |
| 4,620,534 A | 11/1986 | Zartman |
| 4,755,164 A | 7/1988 | Hinzmann |
| 4,891,042 A | 1/1990 | Melvin et al. |
| 4,900,299 A | 2/1990 | Webb |
| 4,921,474 A | 5/1990 | Suzuki et al. |
| 4,923,440 A | 5/1990 | Genaro |
| 4,960,417 A | 10/1990 | Tar, Jr. et al. |
| 5,002,526 A | 3/1991 | Herring |
| 5,041,080 A | 8/1991 | Shimatani et al. |
| 5,080,659 A | 1/1992 | Nakanishi |
| 5,158,535 A | 10/1992 | Paul et al. |
| 5,330,421 A * | 7/1994 | Tarr et al. .................. 604/15 |
| 5,346,468 A | 9/1994 | Campion et al. |
| 5,350,354 A | 9/1994 | Billmers |
| 5,554,108 A | 9/1996 | Browning et al. |
| 5,702,553 A | 12/1997 | Iskra et al. |
| 5,709,652 A | 1/1998 | Hagerty |
| 5,782,793 A | 7/1998 | Nielsen et al. |
| 5,782,794 A | 7/1998 | Downs |
| 5,788,663 A | 8/1998 | Igaue et al. |
| 5,788,664 A | 8/1998 | Scalise |
| D415,565 S | 10/1999 | Hayes et al. |
| 6,171,426 B1 | 1/2001 | Blanchard |

* cited by examiner

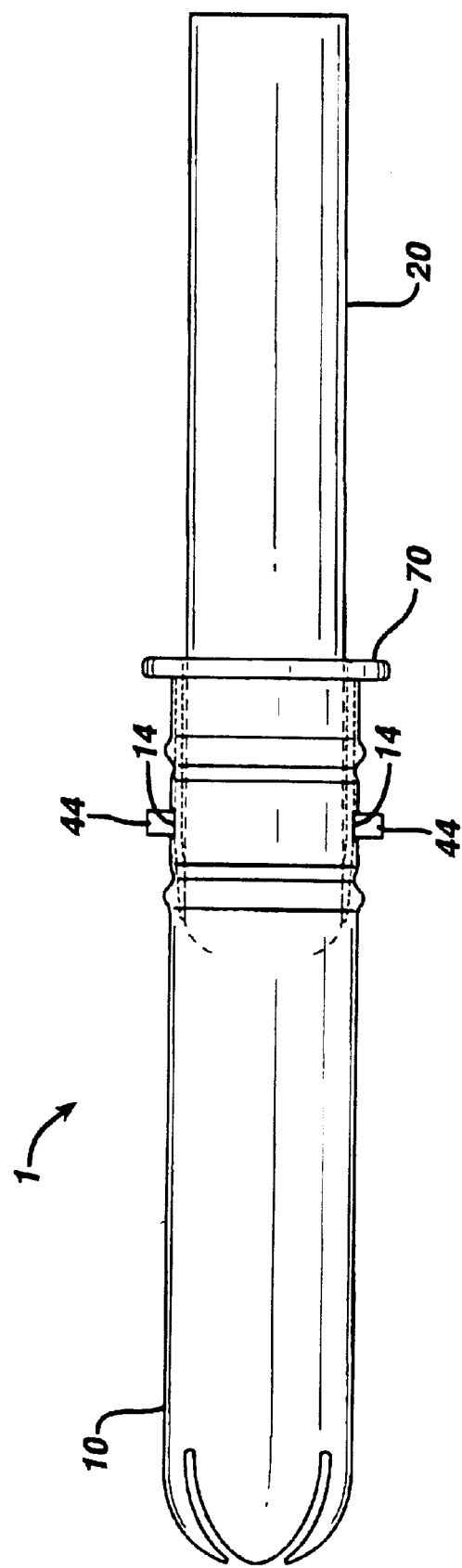

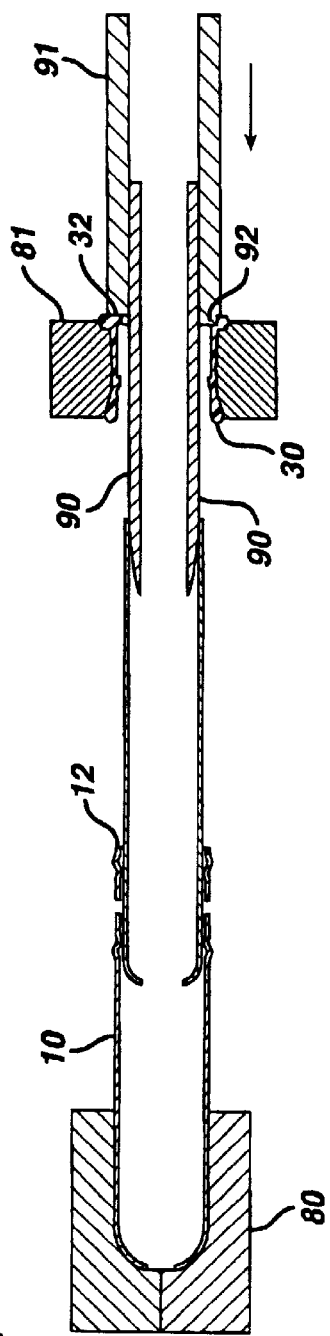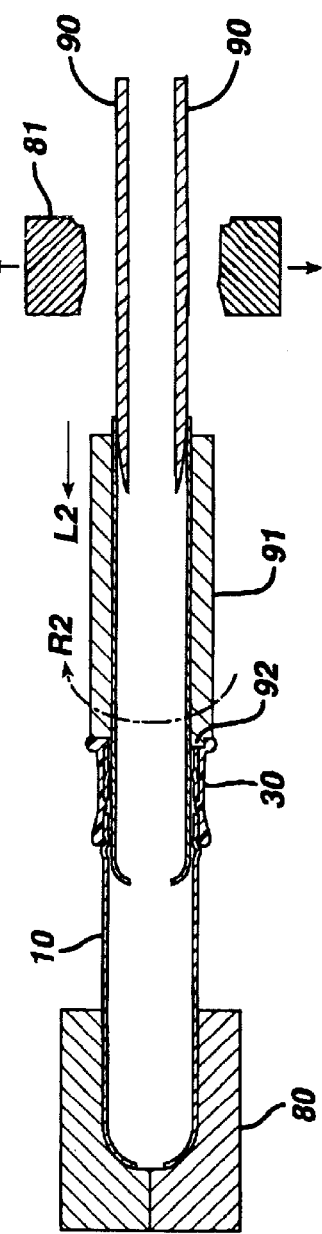

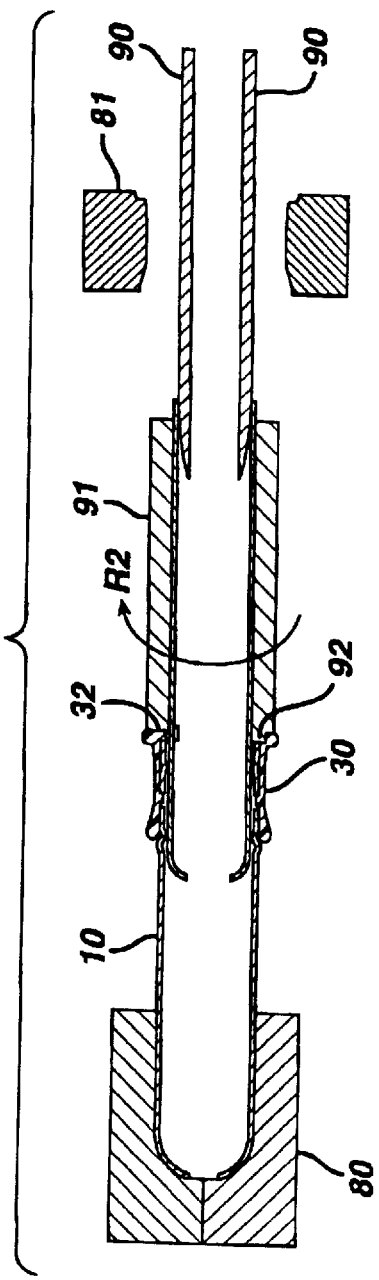
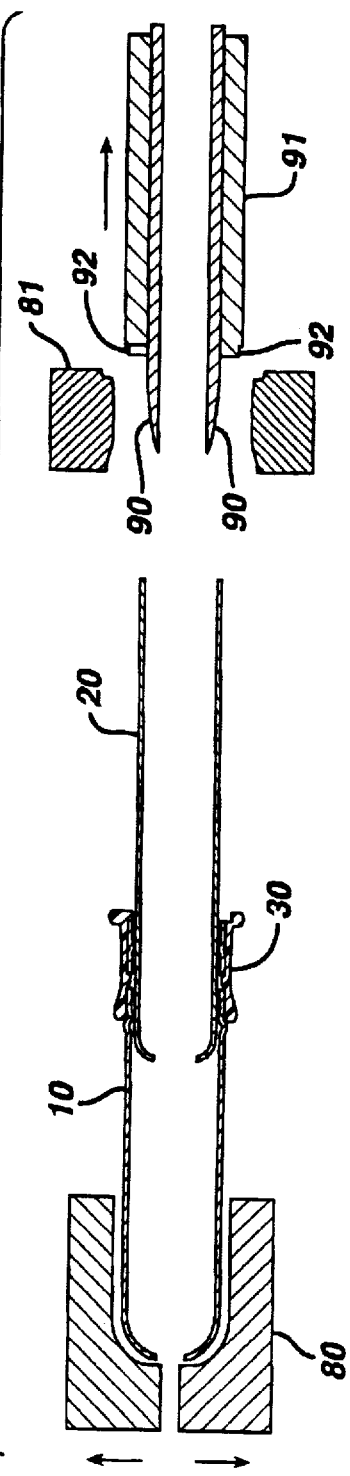

APPLICATOR FOR CATAMENIAL DEVICE HAVING IMPROVED GRIPPER END

FIELD OF THE INVENTION

The present invention provides an applicator comprising a tubular insertion member and a retrofitted gripping member. The applicator is particularly useful for delivering a catamenial device into the vaginal canal, such as a tampon or menstrual collection cup.

BACKGROUND OF THE INVENTION

Applicators for inserting and expelling objects into a body cavity typically comprise a tubular insertion member having an insertion end and a trailing end opposite thereof, and an expulsion member slideable within the tubular insertion member. The trailing end generally incorporates features to allow a user to more or less securely hold the applicator during use—inserting the applicator into a body cavity, expelling a substantially enclosed object contained by the applicator, and withdrawing the applicator from the body. Unfortunately, many applicators known in the art comprise a gripping section that exhibits a weakness during at least one of the three above-identified steps of using the applicator.

Voss, U.S. Pat. No. 4,361,150, and Sartinoranont, U.S. Pat. No. 4,447,222, incorporates projections, such as a ring, at the trailing end of the applicator member. These projections provide resistance to rearward finger slippage during the expulsion step of using an applicator, and they may help the user to remove the applicator from her body.

Whitehead, U.S. Pat. No. 4,508,531, reduces the diameter of the applicator in the vicinity of the tubular insertion member trailing end. The reduced diameter creates a shoulder near the insertion end to resist finger slippage toward the insertion end during the insertion step.

Both of these approaches suffer from providing resistance to finger slippage in only one direction. Efforts to provide resistance in two directions, as disclosed in the art, suffer from shortcomings as well.

First, Voss, U.S. Pat. No. 3,575,169, increases the friction on the trailing end of the tubular insertion member by coating it with pulverized stone or sand. This may be especially helpful as applicator manufacturers are moving toward the use of higher gloss surfaces, which are purported to aid in ease of applicator insertion into a body cavity.

Second, Hagerty, U.S. Pat. No. 5,709,652, employs a plurality of finger-accepting apertures in the applicator to provide relatively abrupt, finger accepting edges. These edges frictionally resist movement of a user's finger in response to longitudinal forces on the device. Although a useful contribution to the art, the finger-accepting edges disclosed by Hagerty, are generally limited to the wall thickness of the applicator.

Finally, Suzuki et al., U.S. Pat. No. 4,921,474, discloses a sanitary tampon applicator comprising a plastic outer sleeve having a diameter-reduced section along a length adjacent its rear end so as to form an annular shoulder, and a annular rib at its rear open end. This device has two or more physical restraints as a means for the user to hold the applicator securely during all of the steps of use. It is noteworthy that the Suzuki applicator is limited to a "plastic" outer sleeve. One skilled in the art would recognize that it would be difficult to form similar physical restraints (shoulder and rib) on a paperboard applicator. Plastic applicators incorporating such design features traditionally employ sophisticated molds and processes in injection molding operations, e.g., comprising split cores and/or side slides. The resulting mold designs and processing steps can add significant costs to the final product.

Accordingly, what is needed, is an applicator that can be manufactured by low-cost, high-speed equipment and retrofitted with a superior gripping member that has features to help during insertion of the applicator into a body cavity, expulsion of a contained object, and withdrawal of the applicator from the body.

SUMMARY OF THE INVENTION

The present invention relates to applicators for inserting objects into body cavities, and to methods for making the same. The applicators are particularly useful for inserting catamenial and prophylactic devices into a vaginal canal. The applicators comprise a tubular insertion member and a retrofitted gripping member affixed to the tubular insertion member.

The tubular insertion member has an insertion end, an oppositely disposed trailing end, and a trailing end outer diameter. The gripping member has an outer diameter greater than a coincident trailing end outer diameter and a raised area. In one preferred embodiment, the gripping member has a length to inner diameter ratio of at least about 0.5. In another preferred embodiment, the gripping member has a length of at least about 5 mm.

The gripping member comprises at least one raised area on its outwardly disposed surface. This raised area resists movement of the user's manual digit in response to longitudinal forces on the insertion member. Longitudinal forces are created during both the insertion step of use, as well as the expulsion step delivering the contained object from the insertion member into the body cavity.

In another embodiment, the present invention relates to an applicator for inserting an object having a gripping member with at least one flexible arm extending from an inner surface thereof. The tubular insertion member trailing end is fitted between the gripping member inner surface and the at least one flexible arm. A tubular expulsion member may be slideably fitted within the trailing end, and this position of the expulsion member urges the flexible arm against the tubular insertion member to provide a more secure device. The flexible arm may also help to prevent the expulsion member from being separated from the insertion member prior to use.

In yet another embodiment, the present invention relates to an applicator having a tubular insertion member as described above with an aperture proximate its trailing end. The applicator also has a gripping member with an annular ring having a flexible arm substantially perpendicular to and extending from an inner peripheral edge of the ring. The flexible arm has a distally located protuberance, and this protuberance extends outwardly from the interior of the tubular insertion member and through the aperture when the gripping member is affixed to the insertion member. The annular ring and the extending protuberance form raised areas that resist movement of a user's manual digit in response to longitudinal forces on the insertion member.

The present invention also provides methods for making applicators having retrofitted gripping members, including affixing gripping members as disclosed above, to the trailing end of a tubular insertion member.

In a preferred embodiment of the present invention, a tubular insertion member is provided having an insertion end and a trailing end and a tubular expulsion member slideable the trailing end. A gripping member is coaxially aligned with the insertion and expulsion members. The tubular insertion member is clamped with a first clamping mechanism, and the gripping member is clamped with a second clamping mechanism. An optional internal stabilizing tool may be passed through the gripping member and into a portion of the expulsion member. A displacement tool, in a telescopic position over the internal stabilizing tool, then engages the gripping member, after which the second clamping mechanism is retracted. Through linear displacement of the displacement tool, the gripping-member is advanced over the expulsion member and onto at least a portion of the tubular insertion member trailing end. Lastly, displacement tool, the internal stabilizing tool, and the first clamping member are all retracted, thereby freeing the assembled applicator for any further processing steps.

BRIEF DESCRIPTION OF THE DRAWINGS

FIG. 11 is a side view of the gripping member in FIG. 10 retrofitted onto a tubular insertion member.

FIGS. 12 12A, 12B is a diagram of steps included in a method of manufacturing applicators provided by the present FIGS. 13 13A, 13B, 13C, 13D, 13E, 13F is a diagram of steps included in a second method of manufacturing applicators provided by the present invention.

DETAILED DESCRIPTION OF THE INVENTION AND THE PREFERRED EMBODIMENTS

Figure 1:
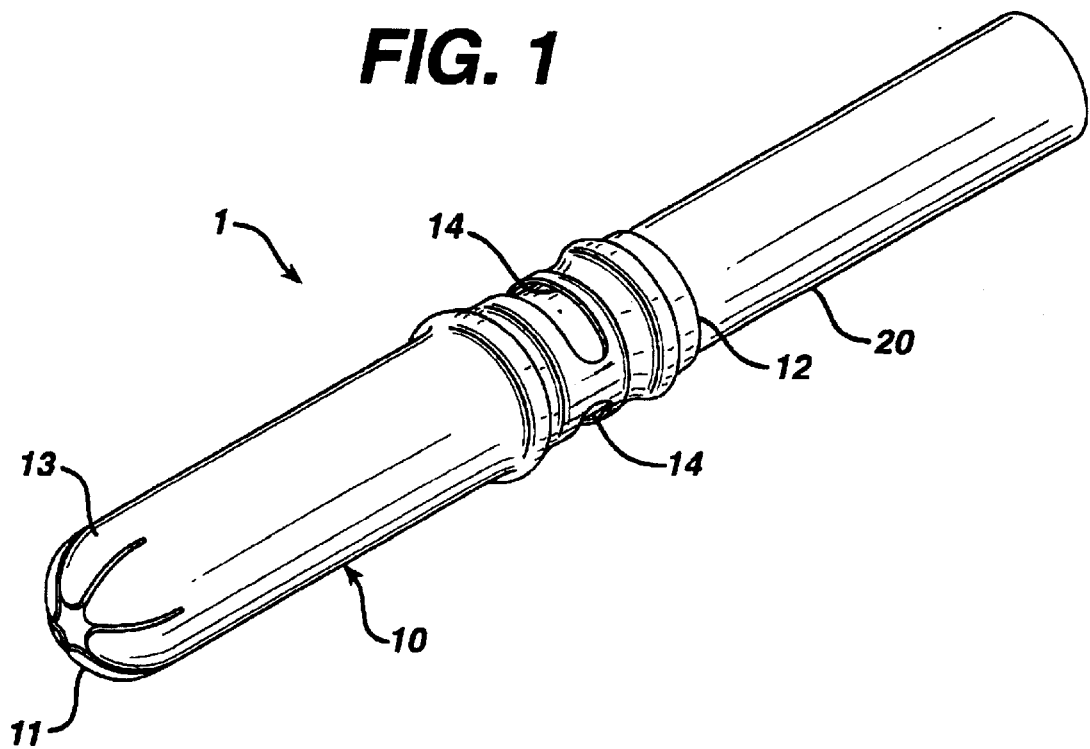
FIG. 1 is a perspective view of an applicator having a tubular insertion end, a trailing end opposite thereof, and a tubular expulsion member slideably fitted within the trailing end.

The present invention provides an applicator comprising a tubular insertion member and a retrofitted, superior gripping member, employing design features that aid in inserting the applicator into a body cavity, expelling a contained object, and withdrawing the applicator from the body. Manufacturing the gripping member separately provides numerous advantages, some of which will be discussed below.

One significant advantage is the versatility of materials and processes available for manufacturing the tubular insertion and expulsion members. Paperboard products appeal to both the manufacturer and the consumer, derived from factors such as ease of manufacture, cost of manufacture, purchase cost, environmental benefits, and flushability convenience. However, their features intended to aid the consumer in handling the product during use have been limited. Embossed rings and finger-accepting apertures are typically confined to the gauge of the paperboard (or combined layers) used. A superior gripping member, manufactured separately, can be retrofitted onto a paperboard tubular insertion member, without significantly eliminating any of the noted appeal.

Insertion and expulsion members are also manufactured from plastic. Generally, commercially available products are made from polyolefins, such as polyethylene, and at least the tubular insertion members of these products are formed through an injection molding process. This process is used to enable the manufacturer to balance key characteristics of the tubular insertion member. Molding inserts and cores are machined to form a tapered product in which the wall thickness in the gripping region is relatively thick to maintain structural stability during the insertion and expulsion steps of use. While the thickness in the insertion end is minimized to provide flexibility and low expulsion force. Injection molding also enables the manufacturer to make uniquely shaped (e.g., curved) tubular insertion members as well as to make gripping features that would be difficult or impossible to achieve using alternative processes. However, there are less sophisticated and less expensive polymer forming techniques, such as extrusion and blow molding, that could be employed if it is not necessary to incorporate complex features into the tubular insertion member, itself. Instead, the more complex features could be separately formed and retrofitted onto such an inexpensively manufactured tubular insertion member.

In this manner, the gripping member itself can provide a substantial portion of the structural stability necessary for inserting and expelling objects into body cavities. Therefore, a minimum amount of paperboard or an extremely thin-walled polymeric tube may be used in conjunction with the gripping member as a complete and useful system. This approach can reduce the cost of manufacture down and eliminate the likelihood that the applicator may collapse during use.

A second advantage offered by separate component manufacturing is realized through the option of using state of the art high-speed equipment, such as disclosed in Hinzmann, U.S. Pat. No. 4,755,164, the disclosure of which is herein incorporated by reference, and commercially available from Hauni Richmond, Inc. of Richmond, Va. Hinzmann employs reservoir systems that accumulate applicator components between major steps of manipulation and assembly. Applicators with any significant projections extending from their outer surfaces will not stack neatly (parallel) in the reservoir systems, thereby reducing the efficiency of space and transfer. Such products may also create process downtime due to-applicators being "hung up" in the accumulators. The reservoir systems provide efficiency in multi-component manufacturing by maintaining continuous overall production even during downtime of an upstream piece of equipment. Manufacture of the tubular insertion member, expulsion member, and e.g., tampons, as well as component assembly, can take place with the gripping member retrofitted as a final step prior to packaging.

One technique that can be employed for affixing a separately manufactured gripping member to a tubular insertion member is to press the gripping member onto one end. This technique necessitates that the gripping member's smallest outer diameter will be greater than the coincident outer diameter of the tubular insertion member it is combined with. As used herein the specification and the claims, the phrase "coincident diameter" (and variants thereof) relates to diameters of two or more elements extending through the same point and along the same line or plane. This size differential creates an interference between the element and provides a visual or a tactile cue of applicator insertion depth, and thereafter object positioning within the body cavity. Greater control and handling is also provided with a gripping member having a greater diameter. Applicators known in the art having reduced diameter gripping regions, do so by "necking down" a portion of the tubular insertion member (see for example Huffman, U.S. Pat. No. 4,573, 964). As the gripping area is reduced, so is the amount of control by the user. Moreover, an expulsion member used with such an applicator will necessarily become small. Consumers have voiced dislikes associated with small expulsion members.

Preferred embodiments of the present invention are illustrated in the figures and corresponding description, wherein like elements are labeled with like numerals. As shown in FIG. 1, applicator 1 comprises a tubular insertion member 10 having an insertion end 11, an opposing trailing end 12, and a tubular expulsion member 20 slideably fitted within the trailing end 12.

The insertion end 11 is preferably substantially closed prior to expulsion of an object contained therein. As can be seen in FIG. 1, one technique for substantially closing the insertion end 11 is by employing a plurality of inwardly curved petals 13. The petals will flex and/or hinge to an open position upon expelling objects contained by the tubular insertion member 10. The number of petals generally ranges from about 4 to about 6. An alternative technique is a pleating process is disclosed in Neilsen et al., U.S. Pat. No. 5,782,793. Alternatively, the insertion end may be more or less open, that is the diameter along the length of the tubular insertion member is substantially equivalent to the diameter of the insertion end. Proctor & Gamble, of Cincinnati, Ohio, currently offers for sale an open-ended tampon applicator under the trade name TAMPAX brand flushable applicator tampons.

The tubular insertion and expulsion members of the present invention can be made from numerous materials generally known to those of ordinary skill in the art, such as plastic (polymers) and paperboard. Plastic applicator members may comprise conventional polymers, such as polyolefins, or be of more sophisticated polymers and polymer blends formulated to provide features such as biodegradability and/or water dispersibility. A representative, non-limiting list of polymers, includes polyolefins, such as polyethylene, and polypropylene; polystyrene, polyvinyl alcohol, polylactic acid, poly(3-hydroxybutyric acid), and combinations thereof. Examples of applicators that are designed to be dispersible or biodegradable are disclosed in Herring, U.S. Pat. No. 5,002,526 and Assenheimer-Downs, U.S. Pat. No. 5,782,794 relating to applicators made from polyvinyl alcohol based compositions, Billmers, U.S. Pat. No. 5,350,354 relating to applicators made from starch based compositions, and Webb, U.S. Pat. No. 4,900,299 relating to applicators made from poly(3-hydroxybutyric acid) based compositions. Plastic members may be made by injection molding, blow molding, extrusion and the like.

Paperboard tubular and expulsion members may be constructed from a single layer of paperboard material, or from a plurality of laminated layers. Useful paperboard stock for the formation of the members includes, without limitation, paperboard, cardboard, cup stock, paper, and the like. The following non-limiting processes may be used for making paperboard applicator components: spiral winding as disclosed in Campion et al., U.S. Pat. No. 5,346,468, convolute winding as disclosed in Whitehead, U.S. Pat. No. 4,508,531, and forming a sheet around a mandrel and then sealing an overlapped seam as disclosed in Hinzmann, U.S. Pat. No. 4,755,164.

Paperboard members may include one or more surface layers, which may be useful to increase the comfort and ease of insertion and withdraw of the applicator. The surface layers may be in the form of laminated films, cured coatings, and the like. An example of such a surface layer is disclosed in commonly-assigned, co-pending application U.S. Ser. No. 09/105,787 filed on Jun. 26, 1998. A representative, non-limiting list of useful materials to be used as the surface layers includes, waxes, cellophane, polyolefins, polyesters, epoxies, and the like. The surface layers may also include thermal stabilizers, pigments, fragrances, surfactants, anti-microbial agents, medicaments, and the like.

There are many techniques known for applying the surface layers. A representative, non-limiting list of such techniques includes spraying, extruding, slot coating, brushing, transfer coating, and the like. Additional processing steps may be required to cure the surface treatments to a useable form other than simple air curing, such as applying irradiation or other forms of energy.

Typical dimensions for each of the tubular insertion and expulsion members include a length of from about 50 to about 100 millimeters, a diameter of from about 8 to about 20 millimeters, and a thickness of from about 0.1 to about 0.6 millimeters. Preferably the insertion and expulsion members are cylindrical tubes that are substantially straight along their lengths. They may however, be of alternative geometry, such as square, elliptical, or triangular. Additionally, the tubular members may be curvilinear along their length to improve comfort and manipulation of the applicator during insertion and withdraw from a body cavity. An example of curved applicator components can be seen in Paul et al., U.S. Pat. No. 5,158,535.

Figure 2:
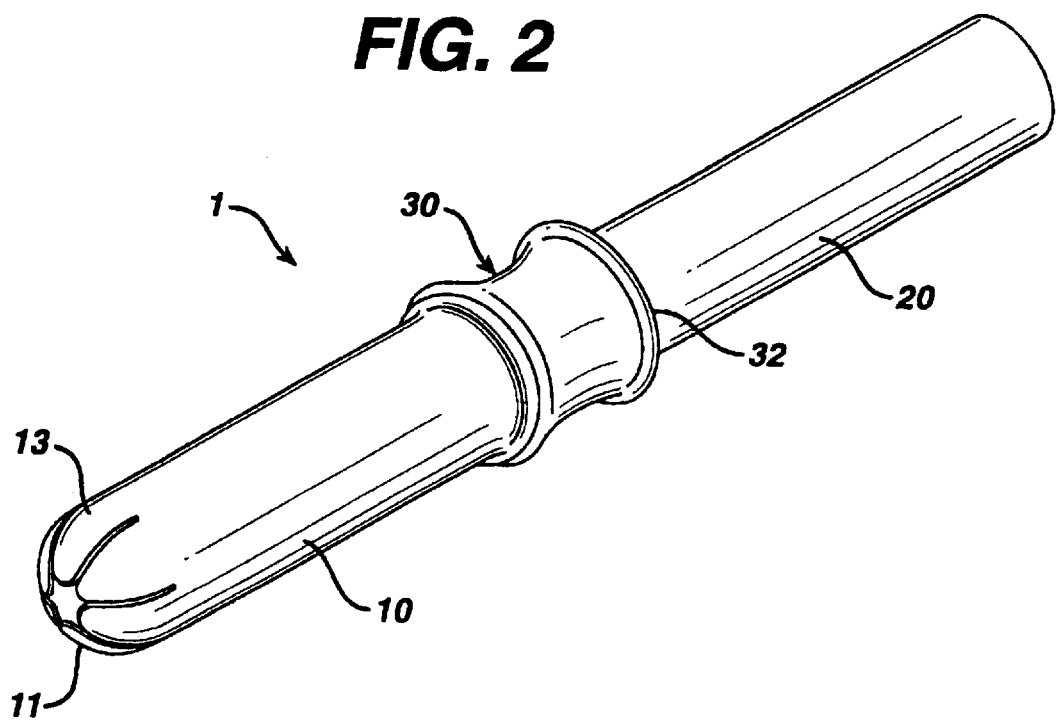
FIG. 2 is a perspective view of the applicator in FIG. 1 having a gripping member retrofitted onto the trailing end of the tubular insertion member.
Figure 3:
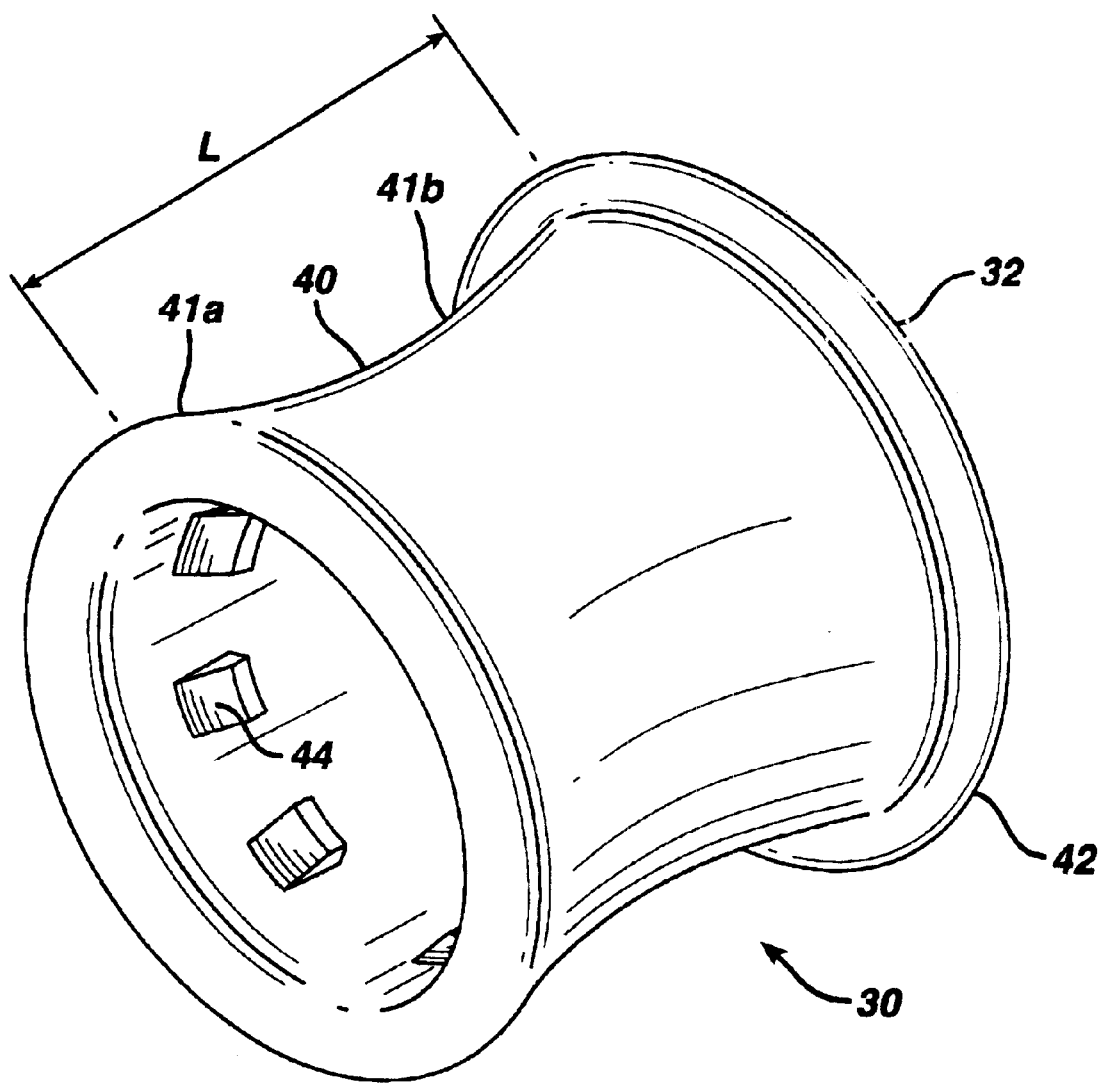
FIG. 3 is a perspective view of a preferred gripping member.

Referring to FIG. 2, applicator 1 further comprises a gripping member 30, which is manufactured separately from the insertion and expulsion members and thereafter affixed, preferably immovably, to at least a portion of the trailing end of the tubular insertion member.

FIGS. 2–6 depict a preferred embodiment of the gripping member 30, having a minimum outer diameter 31, a length "L", and an intermediate area 40 disposed between two longitudinally separated raised areas 41a and 41b. The curvilinear transition between the intermediate area and the two raised areas preferably forms a "saddle-shaped" profile. This profile provides comfort and control by corresponding to the natural curvature of a user's manual digits (thumb and fingers). A distally located optional flange 42 is also depicted in the figures. The flange 42 provides a structure for the user to grasp to withdraw the insertion member from a body cavity.

The gripping member length "L" is at least about 5 millimeters, and preferably at least about 10 millimeters. Such a length of the gripping member allows the user to grasp the gripping member, rather than placing her manual digits (e.g., fingers) on either side of it. The gripping member should be of sufficient length, such that the utility of design features employed to provide resistance to movement of the user's fingers, is not compromised. For example, if the length of the gripping member is capable of accepting the user's manual digits, especially between longitudinally separated raised areas, it becomes less likely that the user's fingers, etc., would span the distance between these raised areas and lose the benefits of the present invention. Such a distance "D" is preferably at least about 0.35 inches (about 9 mm), more preferably about 0.4 to about 0.6 inches (about 10 mm to about 15 mm).

We have learned that consumers would like to have small diameter applicators while not compromising absorbency. This improves comfort while inserting the device. However, as the diameter of the applicator decreases, user control correspondingly decreases. In an effort to ensure that the gripping member has sufficient area to grasp during use, especially with relatively small diameter insertion members, the gripping member preferably has a length to diameter ratio of at least about 0.5.

Figure 4:
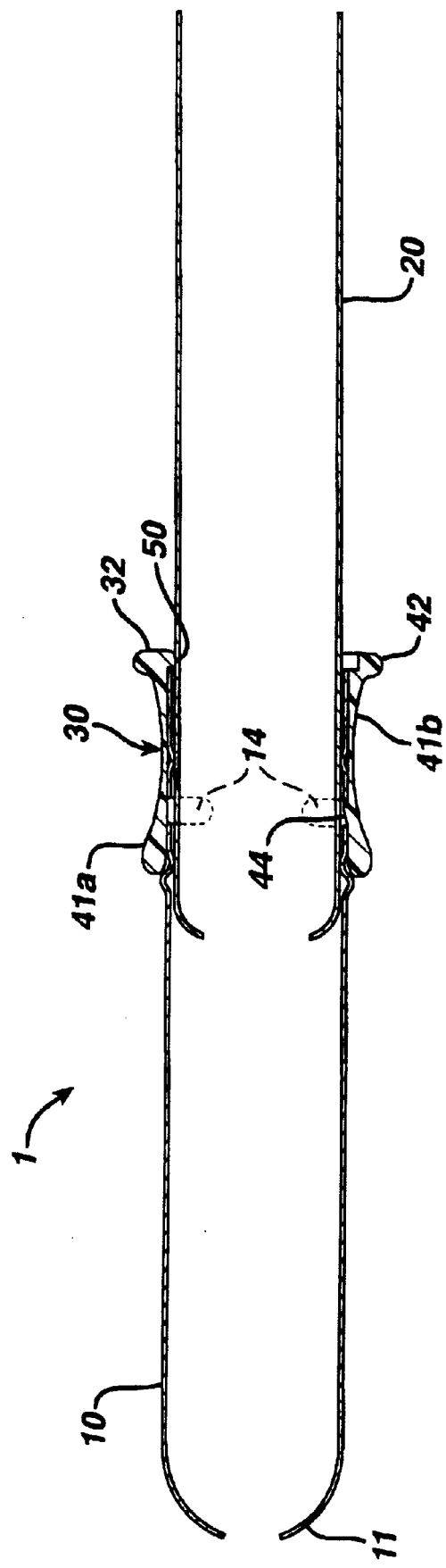
FIG. 4 is a cross-sectional view of the applicator in FIG. 2.

A series of optional protuberances 44 are also shown in the figures. These improve the fixation of the gripping member to the tubular insertion member. The tubular insertion member may employ a cavity proximal its trailing end, such as an aperture 14 shown in FIG. 1, which is capable of receiving one or more of the protuberances 44. The cavity may be any generally concave feature that is capable of receiving the protuberances, examples including embossed regions and apertures. The cross-sectional view in FIG. 4 illustrates the protuberances 44 residing in a portion of two apertures 14 as taught in Hagerty, U.S. Pat. No. 5,709,652, the disclosure of which is herein incorporated by reference. The protuberances may be designed such that they provide additional resistance to separation of the gripping member from the tubular insertion member. For example, the protuberances may be triangulated, or comprise a barb, wherein an apex or barb is capable of pressing into a surface of the tubular insertion member. "Pressing into" may include creating indentations, ruptures, gouges and the like.

Figure 5:
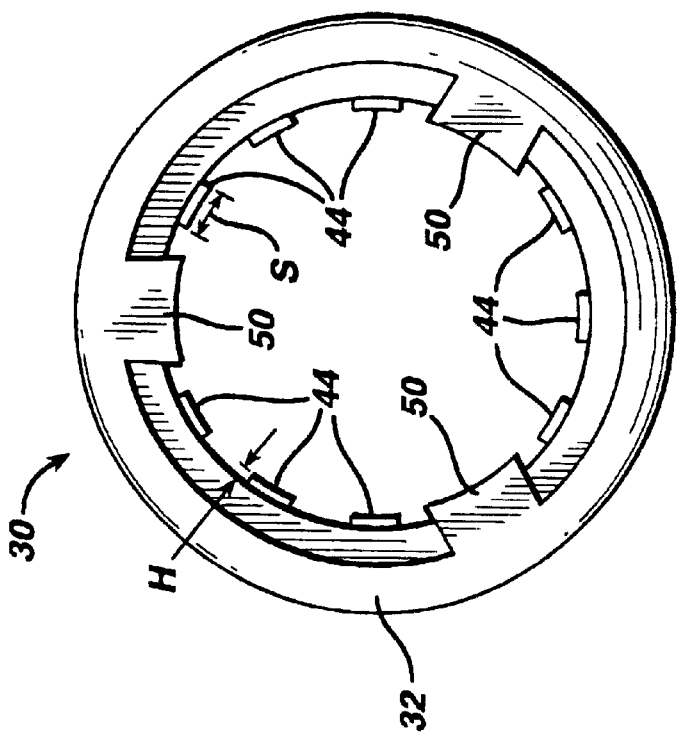
FIG. 5 is an end view of the gripping member shown in FIG. 3, depicting a plurality of the protuberances and stops.
Figure 6:
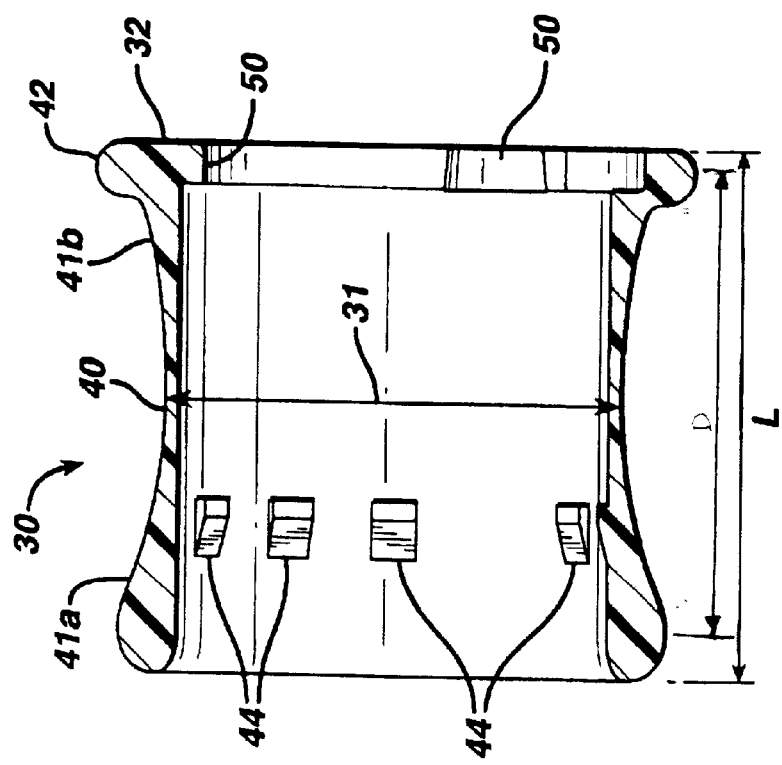
FIG. 6 is a cross-sectional view taken from FIG. 5.

Referring now to FIGS. 5 and 6, preferably the gripping member has from about 2 to about 12 protuberances, and more preferably from 3 to 9. The protuberances have a height "H". It may be helpful in some constructions to relate the height of the projection to the thickness of the material forming the tubular insertion member, the manner of attachment of the gripping member, and the relative outside diameter of the tubular member trailing end and the inside diameter of the gripping member. In a press fit attachment, the height "H" is preferably at least about 0.0005 inches (about 0.01 mm), more preferably at least about 0.001 inches (about 0.03 mm). In a mechanical latch attachment, the height "H" may be at least about 0.003 inches (about 0.08 mm), more preferably, at least about 0.005 inches (about 0.1 mm), and most preferably about 0.01 to about 0.02 inches (about 0.3 to about 0.5 mm). The protuberances may have an arc "S" of at least about 0.5 degrees, preferably, in a mechanical latch attachment manner as disclosed in e.g., FIGS. 3–7, an arc of about 3 to about 10 degrees, and most preferably about 5 to about 7 degrees.

The gripping member 30 may optionally have at least one stop 50 extending inwardly from a trailing edge 32, the edge of the gripping member 30 that is the furthest from the insertion end 11 of the tubular insertion member, as assembled. The stop is capable of maintaining the gripping member at the trailing end of the tubular insertion member. A preferred embodiment has nine protuberances and three stops. Additionally, FIGS. 5 and 6 illustrate the preferred out of phase positional relationship of the protuberances 44 and the stops 50. This positioning provides the attractive option of using simpler injection molding processes and equipment.

While the figures show a gripping member being affixed to the tubular insertion member overlying a portion of the insertion member trailing end, it may also abut the trailing end of the tubular insertion member. It is likely that an abutting gripping member would not require the protuberances and stops described above.

Figure 7:
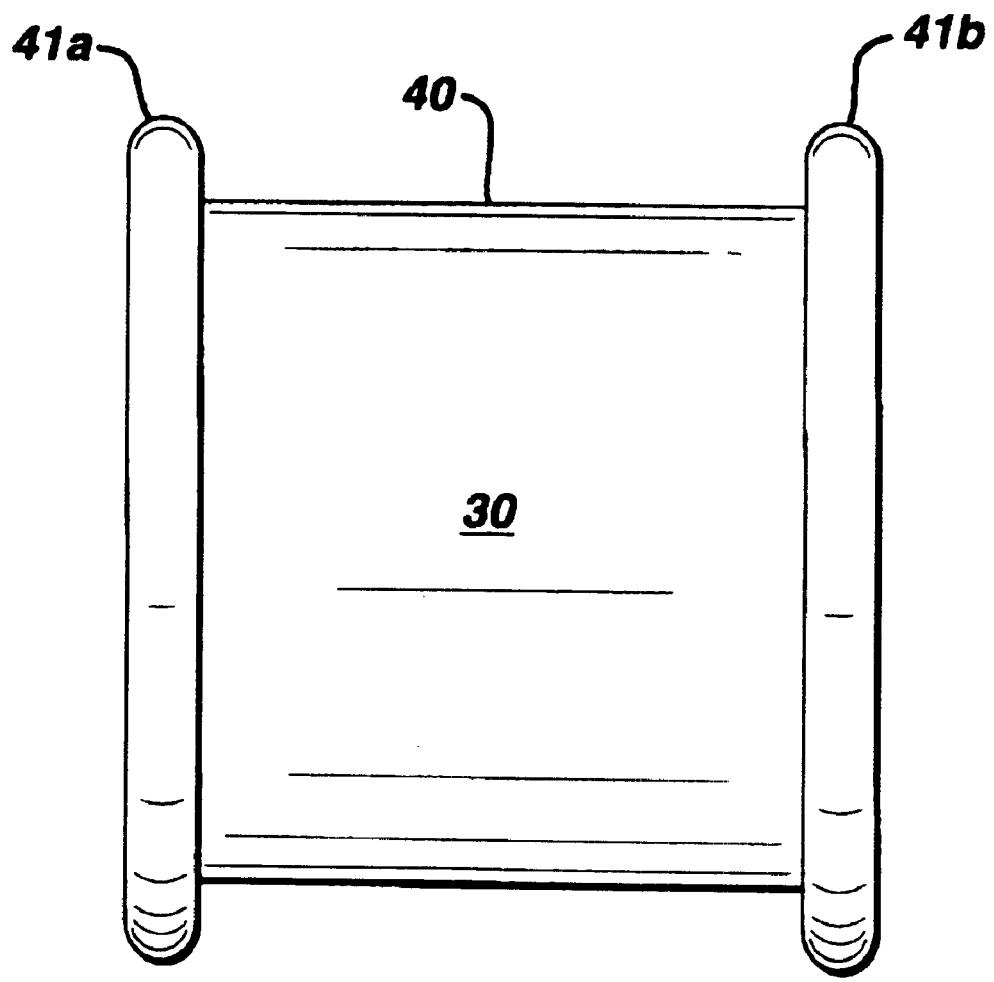
FIG. 7 is a side view of a gripping member having two distally located flanges.

The gripping member 30 illustrated in FIGS. 2–6 has a curvilinear outer profile, generally "saddle" shaped, wherein the two raised areas 41a and 41b are created by the increasing outer diameters towards the edges of the gripping member. An alternative gripping member outer profile is depicted in FIG. 7, wherein the intermediate area 40 has a flat profile yielding a constant outer diameter along the length, with the two raised areas 41a and 41b being formed by longitudinally separated flanges.

Additional outer profiles are possible, wherein the outer surface has at least one raised area that is capable of providing resistance to movement of a user's manual digit in response to longitudinal forces on the tubular insertion member. All of the figures depict the gripping member having two raised areas separated by an intermediate area; however, a single raised area in conjunction with the other specified design features may be sufficient for the utility of the present invention.

Figure 8:
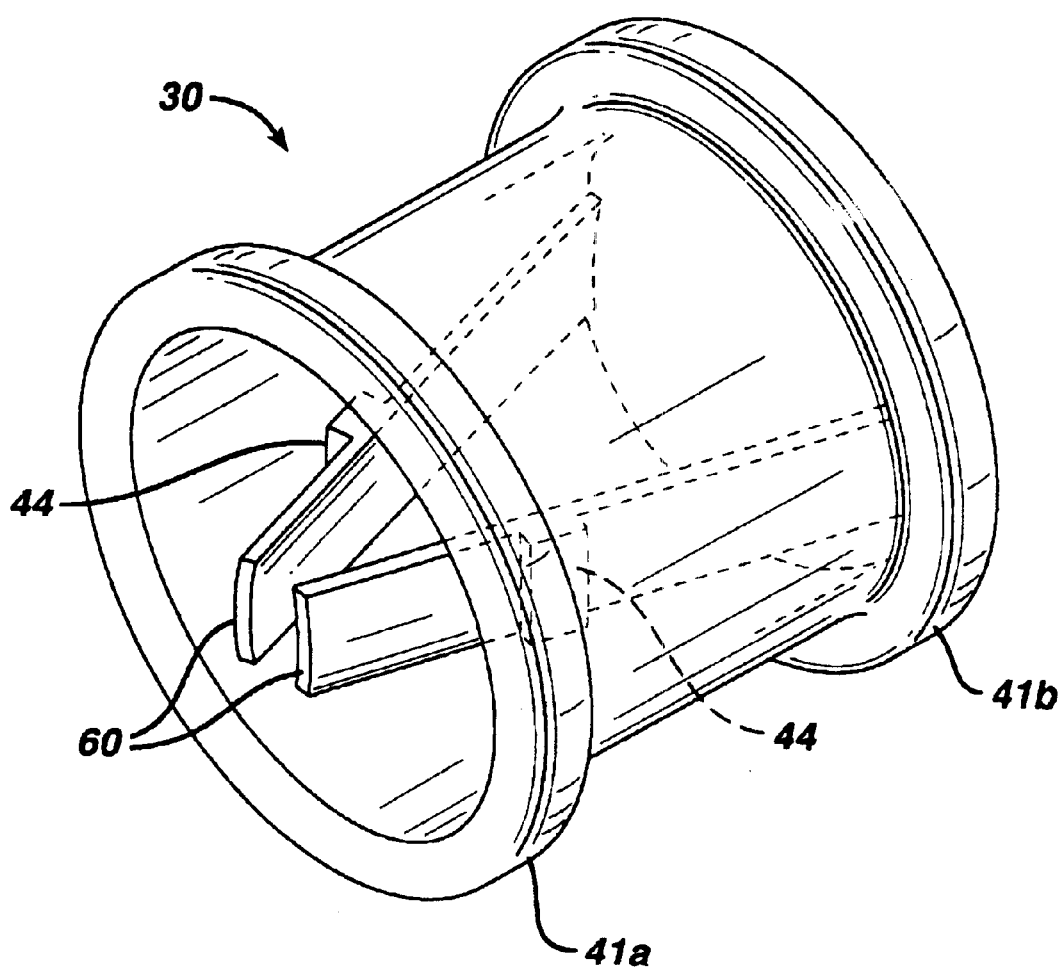
FIG. 8 is a perspective view of a second preferred gripping member employing optional internal flexible arms.
Figure 9:
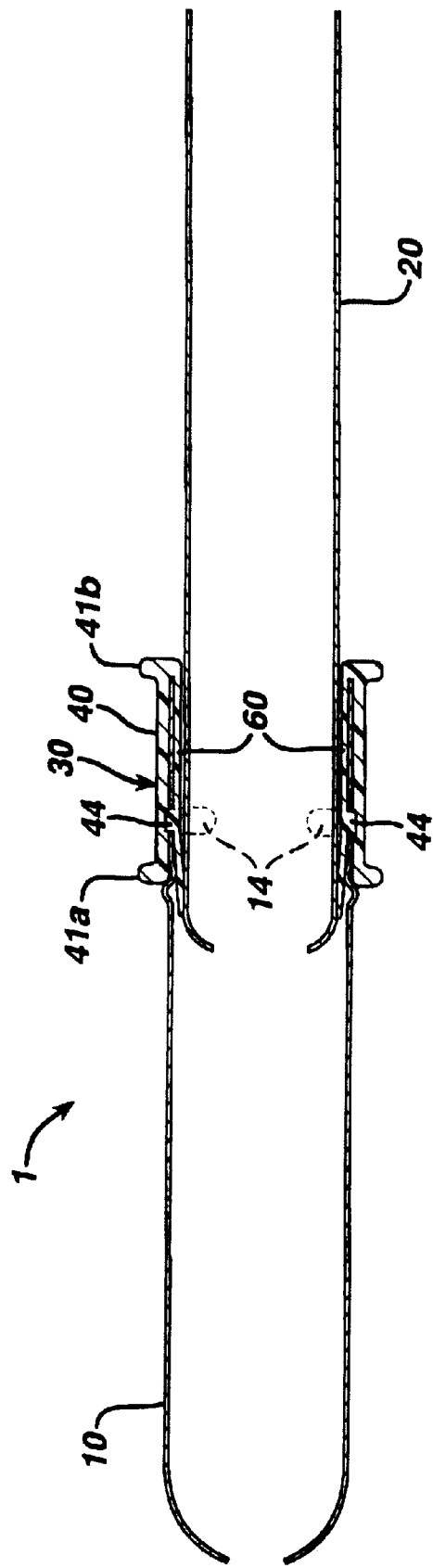
FIG. 9 is a cross-sectional view of the gripping member in FIG. 8 retrofitted onto a tubular insertion member.

To improve the fixation of the gripping member to the tubular insertion member, the gripping member may employ optional design features that reside within the tubular insertion member trailing end. Referring now to FIGS. 8 and 9, the gripping member 30 may optionally comprise one or more flexible arms 60 connected to its inner surface. The tubular insertion member is fitted between the gripping member inner surface and the flexible arms. In this embodiment, protuberances 44 reside on the flexible arms 60. The protuberances 44 may be positioned within tubular insertion member apertures 14 as shown in FIG. 9. Alternatively, retrofitting to tubular insertion members not employing apertures, the protuberances may incorporate design features capable of pressing into the tubular insertion member inner wall to offer a more secure fit.

Figure 10:
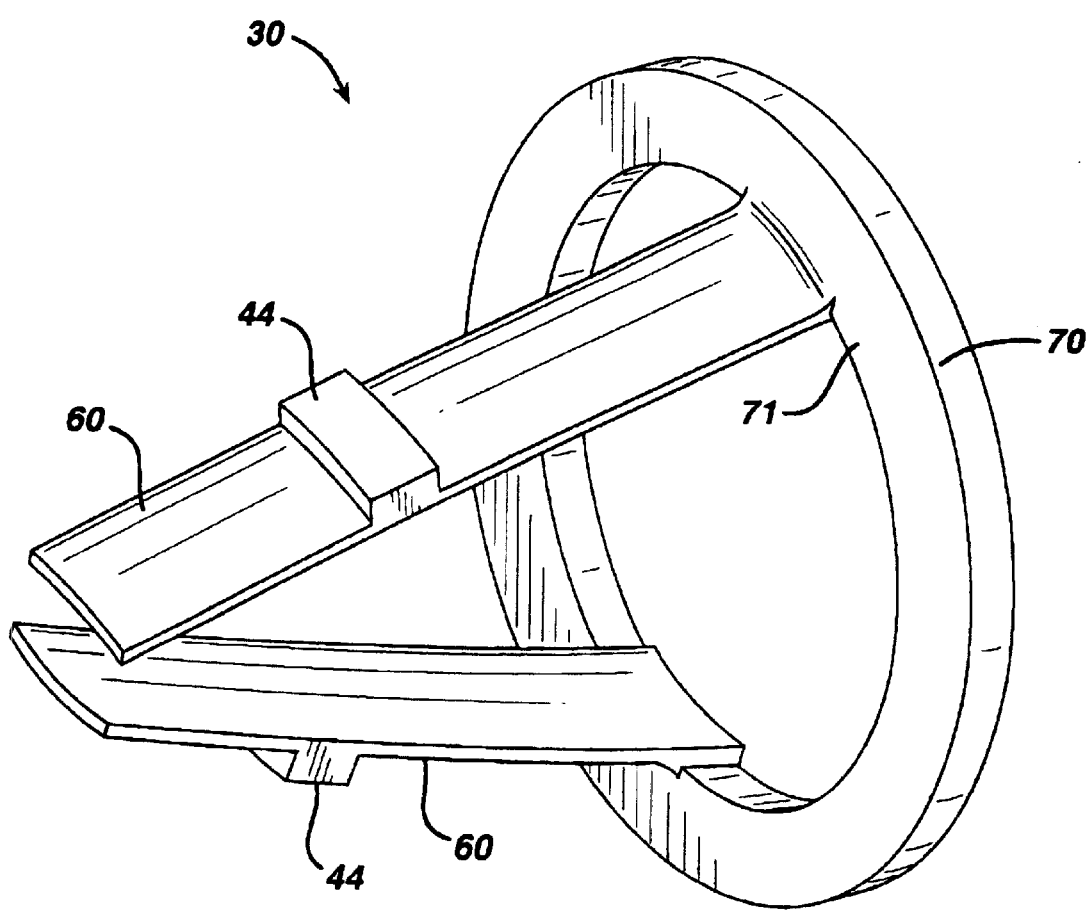
FIG. 10 is a perspective view of a third preferred gripping member comprising an annular ring having flexible arms extending therefrom.

Another embodiment contemplated by the present invention is shown in FIG. 10. This embodiment minimizes both the cost and the environmental impact, due to a reduction in material required. The gripping member 30 comprises an annular ring 70 and one or more flexible arms 60 extending from an inner peripheral edge 71. The annular ring provides resistance to rearward finger movement during the expulsion step of using the applicator. Referring now to FIG. 11, to provide resistance in the opposite direction, a tubular insertion member 10 with apertures 14 proximal its trailing end is used, and protuberances 44, distally located on the flexible arms, are capable of extending therethrough.

Materials useful for the manufacture of the gripping member include the following, non-limiting, representative materials: paperboard, paper, polymeric material, foam, and combinations thereof. Particularly useful polymeric materials include polyethylene, polypropylene, polystyrene, polyvinyl alcohol, polylactic acid, poly(3-hydroxybutyric acid), rubber and other elastomers, and combinations thereof. The gripping member may optionally comprise an additive, either through incorporation into the manufacturing materials, or added to the component through a subsequent processing step. A representative, non-limiting list of additives includes fragrance, odor-neutralizing agents, bacteriostats, bacteriocides, and moisturizers.

The gripping member can be made from any known techniques in the art. Injection molding and blow molding are two such methods useful for making the gripping member from a polymer. Alternatively it can be constructed with paperboard, wherein paper mache techniques are useful. Similar methods of manufacture to that of the tubular insertion member can be used for making the gripping member from paperboard, wherein additional steps are employed to form the along length diameter differential, such as rolling or folding the distal part of the first and second section.

The gripping member outer surface may optionally comprise friction-enhancing means, such as tacky coatings, etched patterns, and the like. Such coatings and/or treatments may be evenly distributed about the outer surface, or they may be restricted to or concentrated in certain, desired portions. The gripping member may be transparent or opaque, and it may be pigmented, as desired. Where a range of differing products is offered to the consumer, the gripping member can be color-coded to indicate a particular product.

The present invention also provides methods for making applicators having retrofitted gripping members, such as those described in relation to FIGS. 1–11. Generally the gripping member may be pressed onto a portion of the tubular insertion member and maintained in its position through the dimensions of each component. Preferably, design features as described above such as protuberances, flexible arms, and stops are employed to help secure the gripping member to the tubular insertion member. Beyond these features, other mechanical features such as suction cups, chemical adhesives, and thermoplastic welding techniques may be used to affix the gripping member or to enhance the fit between the gripping member and the tubular insertion member.

Typical applicators comprise both a tubular insertion member and an expulsion member slideably fitted therein into an opening at the trailing end thereof. The process of assembling the two components, as well as filling the tubular insertion member with an object can vary significantly. Accordingly, the gripping member may be fitted onto a portion of the tubular insertion member prior or after assembly, prior or after filling, and fitted from either end of the tubular insertion member. A detailed description of the preferred methods of making the applicators of the present invention, including the steps and sequencing follows.

Figure 12A:
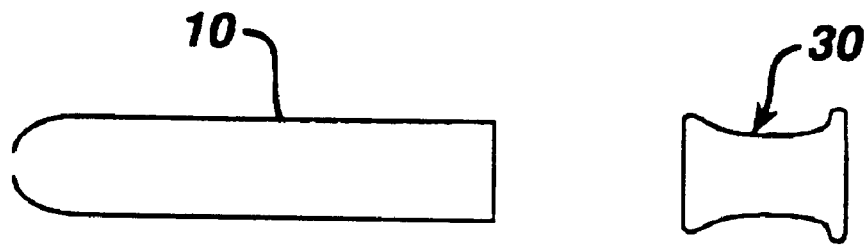
Figure 12B:
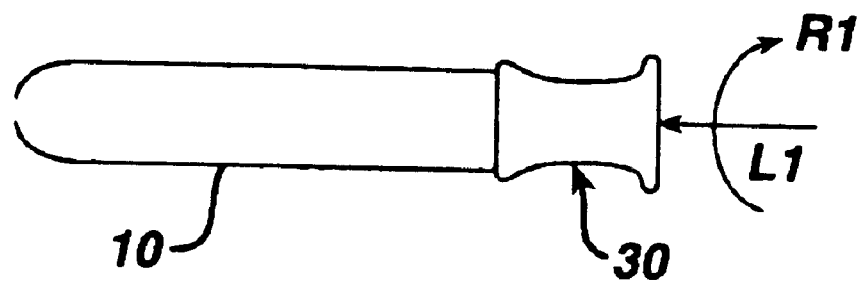

FIG. 12 illustrates a method for making an applicator comprising the step of pressing preferred gripping member 30 onto a portion of the tubular insertion member trailing end 12 through the use of both linear displacement L1, and optional rotational displacement R1. The rotational displacement can occur simultaneously with and/or after the linear displacement. The optional rotational displacement is at least about 0.5 degrees, preferably at least about 5 degrees, and more preferably from about 10 to about 45 degrees.

Figure 13A:
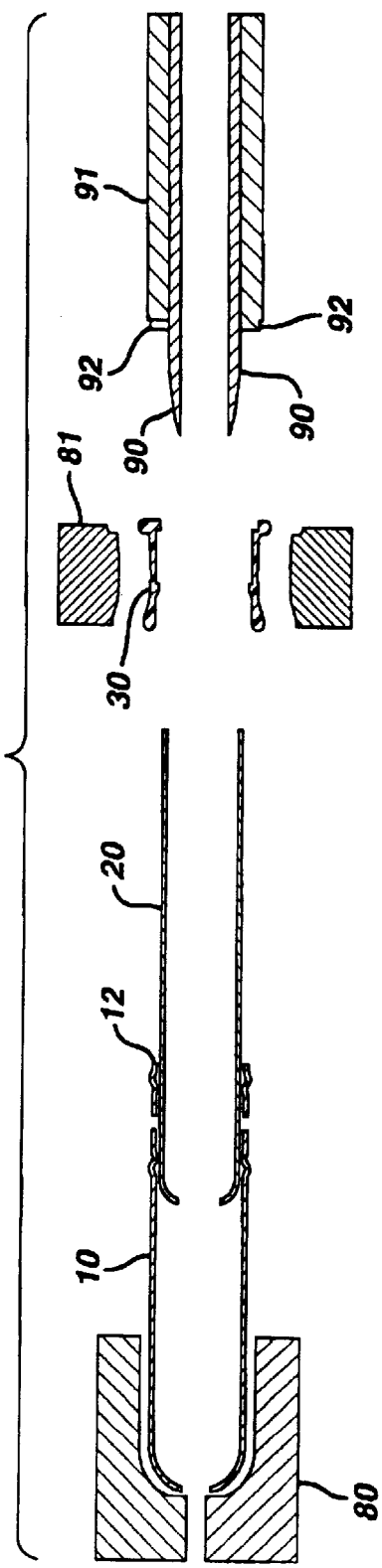
Figure 13B:
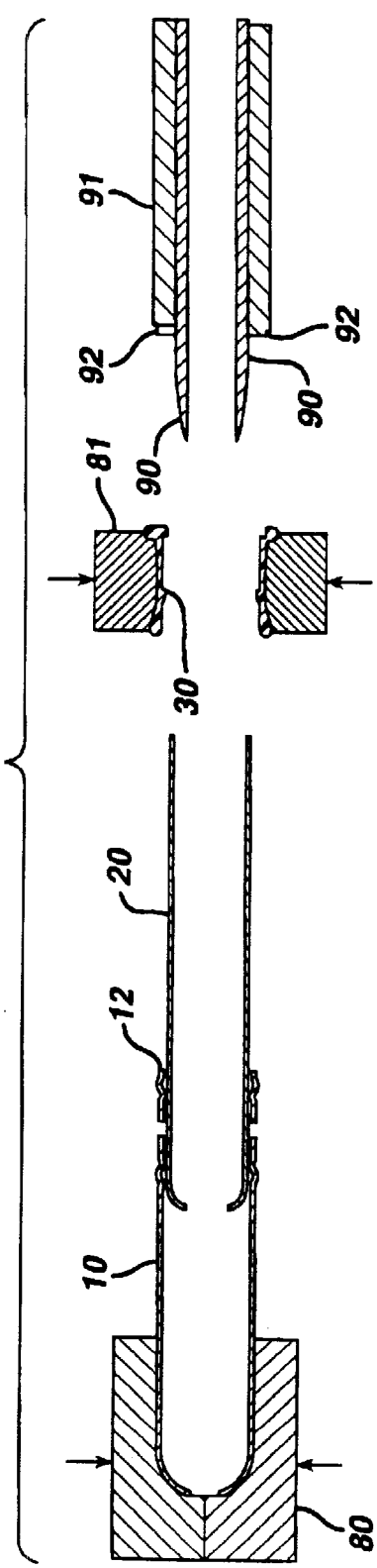

Referring to FIG. 13, another method for making an intravaginal applicator comprises the steps outlined below. A typical tubular insertion member 10 is provided, having an insertion end 11 and a trailing end 12. Slideably fitted within an opening at the trailing end is a tubular expulsion member 20. An object such as a tampon (not shown) for insertion into a body cavity may be loaded in the tubular insertion member from the trailing end prior to assembling the expulsion member with the tubular insertion member, or alternatively be loaded from the insertion end. If the latter method is used, then any closing of the insertion end will take place thereafter, such as through a post-doming process. A gripping member 30 is provided and coaxially aligned with the insertion and expulsion members. The tubular insertion member is clamped with a first clamping mechanism 80, and the gripping member is clamped with a second clamping mechanism 81. Useful clamping or holding mechanisms will be recognized by one ordinarily skilled in the art. For example, a two-sided clamp comprising a surface capable of conforming to the outer geometry of the insertion and gripping members can be used. An optional internal stabilizing tool 90 is passed through the gripping member and into a portion of the expulsion member. A displacement tool 91 may engage the gripping member, and the second clamping mechanism may be retracted. In a preferred embodiment illustrated in FIG. 13, the internal stabilizing tool 90 may be held within the displacement tool 91 in a telescopic arrangement. Through linear motion L2 of the displacement tool, the gripping member is advanced over the expulsion member and onto at least a portion of the tubular insertion member trailing end. Lastly, the displacement tool, the optional internal stabilizing tool, and the first clamping member are all retracted, thereby freeing the assembled applicator 1 for any further processing steps. The sequencing of the steps may be altered to some degree without departing from the spirit and scope of the present invention.

Beyond those steps described above, additional procedures may be included in an assembly process. First, the step of advancing the gripping member onto the tubular insertion member trailing end may comprise both linear L2 and rotational displacement R2. To accomplish this optional step, the displacement tool comprises at least one prong 92 capable of juxtaposition with an at least one stop (shown as element 50 in FIGS. 5 and 6) extending inwardly from a bottom edge of the gripping member. Rotation of the displacement tool will then correspond to rotation of the gripping member.

Second, because the gripping member may employ protuberances extending from an inner surface, the gripping member may be further manipulated to take advantage of these protuberances. For example, the protuberances preferably press into the inner surface of the insertion member to create indentations or "tracks" as the gripping member is pressed on. In an effort to maximize the utility of the protuberances, the gripping member may be rotated, labeled as rotational displacement R2, once it has completed its linear transition onto the tubular insertion member is completed. The minimum rotational displacement required, preferably, is an amount slightly greater than the arc length of the protuberances. An upper range of rotational displacement will be apparent as multiple protuberances are used, that is, the displacement should not be to the extent of removing a protuberance from one track and placing it into another. When tubular insertion members comprise apertures proximate their trailing end, the rotational displacement will also help to align the protuberances with those apertures.

Finally, another method contemplated by the present invention includes connecting multiple components together in a manner to collectively form a gripping member circumscribing the trailing end of the tubular insertion member. This may be desirable, because to injection mold this part as a single component, a mold having side action (side slides) would usually be used. This side action increases the cycle times and decreases the amount of parts per mold area, both of which increase the costs per part.

An example of a multicomponent gripping member could be dividing the gripping member illustrated in FIGS. 2–6 into two separate rings separable, e.g., at the diameter line indicated as 31 in FIG. 6. The rings may employ coupling design features, such as mating male and female elements that are capable of fitting together to affix the gripping member to the tubular insertion member.

An alternative design may separate the gripping member into two or more elements that could "clamp" the tubular insertion member. Such a gripping member could be separated into two halves defined by a plane extending from line "L" in FIG. 3.

An advantage, when using injection molding processes for manufacture, provided by the concept of manufacturing multicomponent gripping members allows sophisticated design features to be included without the necessity of sophisticated molds. The mulicomponent gripping members can be molded in more economical single action molds.

The applicator of the present invention can be used for the delivery of intravaginal objects, such as tampons, menstrual collection devices, and contraceptives. Further, the applicator can be used for delivery of various other materials including, medicaments, moisturizers, vitamins and minerals, spermicides, and odor controlling agents. These materials may be in the form of solids, creams, foams, gels, and the like.

The applicators can be packaged with other non-like or like products, and used as a system of products to satisfy individual consumer needs. In particular, the applicators can be packaged with externally worn or used absorbent products, such as a sanitary napkins, pantiliners, and interlabial pads.

The specification and embodiments above are presented to aid in the complete and non-limiting understanding of the invention disclosed herein. Since many variations and embodiments of the invention can be made without departing from its spirit and scope, the invention resides in the claims hereinafter appended.

What is claimed is:

1. An applicator for inserting an object into a body cavity, comprising:
   a) a tubular insertion member having an insertion end, an oppositely disposed trailing end and a trailing end outer diameter; and
   b) a gripping member affixed to the tubular insertion member trailing end having an outer diameter greater than the coincident trailing end outer diameter and a maximum outer diameter greater than a maximum outer diameter of the tubular insertion member, a length to inner diameter ratio of at least about 0.5, a first raised area and a second raised area separated from the first raised area longitudinally by an intermediate area having a diameter less than that of each of the raised areas, and a trailing edge disposed distal the insertion end of the tubular insertion member.

2. The applicator of claim 1 wherein the intermediate area has a length of at least about 9 mm.

3. The applicator of claim 1 wherein the gripping member comprises curvilinear transitions between the intermediate area and the two raised areas.

4. The applicator of claim 1 wherein the gripping member comprises a flange at the trailing edge.

5. An applicator for inserting an object into a body cavity, comprising:
   a) a tubular insertion member having an insertion end, an oppositely disposed trailing end and a trailing end outer diameter; and
   b) a gripping member affixed to the tubular insertion member trailing end having an outer diameter greater than the coincident trailing end outer diameter, a length to inner diameter ratio of at least about 0.5, a raised area, and a trailing edge disposed distal the insertion end of the tubular insertion member, as assembled;
   wherein the gripping member comprises a protuberance extending from an inner surface arranged and configured to press into an inner surface of the tubular insertion member, and the tubular insertion member comprises a cavity proximate the trailing end that is arranged and configured to receive the protuberance.

6. An applicator for inserting an object into a body cavity, comprising:
   a) a tubular insertion member having an insertion end, an oppositely disposed trailing end having a stop extending inwardly therefrom and a trailing end outer diameter; and
   b) a gripping member affixed to the tubular insertion member trailing end having an outer diameter greater than the coincident trailing end outer diameter, a length to inner diameter ratio of at least about 0.5, a raised area, and a trailing edge disposed distal the insertion end of the tubular insertion member, as assembled;
   wherein the gripping member comprises a protuberance extending from an inner surface arranged and configured to press into an inner surface of the tubular insertion member.

7. The applicator of claim 6 wherein the inner diameter of the gripping member terminating at the stop is less than the coincident trailing end outer diameter.

8. The applicator of claim 6 wherein the gripping member has a plurality of protuberances and stops.

9. An applicator for inserting an object into a body cavity, comprising:
   a) a tubular insertion member having an insertion end, an oppositely disposed trailing end and a trailing end outer diameter; and
   b) a gripping member comprising polymeric foam affixed to the tubular insertion member trailing end having an outer diameter greater than the coincident trailing end outer diameter, a length to inner diameter ratio of at least about 0.5, a raised area, and a trailing edge disposed distal the insertion-end of the tubular insertion member.

10. An applicator for inserting an object into a body cavity, comprising:
    a) a tubular insertion member having a trailing end and a trailing end outer diameter; and
    b) gripping member affixed to the tubular insertion member trailing end having an outer diameter greater than the coincident trailing end outer diameter and a maximum outer diameter greater than a maximum outer diameter of the tubular insertion member, a length of at least about 5 millimeters, a raised area, and a trailing edge disposed distal the insertion end of the tubular insertion member, as assembled;
    wherein the gripping member has two raised areas separated longitudinally by an intermediate area having a diameter less than that of each of the raised areas.

11. The applicator of claim 10 wherein the intermediate area has a length of at least about 9 mm.

12. The applicator of claim 10 wherein the gripping member comprises curvilinear transitions between the intermediate area and the two raised areas.

13. An applicator for inserting an object into a body cavity, comprising:
    a) a tubular insertion member having a trailing end and a trailing end outer diameter; and
    b) gripping member affixed to the tubular insertion member trailing end having an outer diameter greater than the coincident trailing end outer diameter, a length of at least about 5 millimeters, a raised area, and a trailing edge comprising a flange disposed distal the insertion end of the tubular insertion member.

14. An applicator for inserting an object into a body cavity, comprising:
   a) a tubular insertion member having a trailing end; and
   b) a gripping member having at least one flexible arm extending from an inner surface thereof;
   wherein the tubular insertion member trailing end is fitted between the gripping member inner surface and the at seat one flexible arm.

15. The applicator of claim 14 further comprising a tubular expulsion member slideably fitted within the tubular insertion member trailing end, wherein the expulsion member is arranged and configured to urge the at least one flexible arm against the tubular insertion member.

16. The applicator of claim 14 wherein the gripping member has an outwardly disposed raised area.

17. The applicator of claim 16 wherein the gripping member has two raised areas separated longitudinally by an intermediate area having a diameter less than that of each of the raised areas.

18. An applicator for inserting an object into a body cavity, comprising:
   a) a tubular insertion member having a trailing end and an aperture proximate the trailing end extending from an outer surface to an inner surface thereof; and
   b) a gripping member comprising an annular ring, a flexible arm substantially perpendicular to and extending from an inner peripheral edge of the annular ring, the flexible arm having a distally located protuberance;
   wherein the flexible arm is fitted within the tubular insertion member trailing end, and the protuberance extends through the aperture.

* * * * *